(12) United States Patent
Barber et al.

(10) Patent No.: US 12,080,184 B2
(45) Date of Patent: Sep. 3, 2024

(54) MIXED-REALITY ENDOSCOPE AND SURGICAL TOOLS WITH HAPTIC FEEDBACK FOR INTEGRATED VIRTUAL-REALITY VISUAL AND HAPTIC SURGICAL SIMULATION

(71) Applicant: ARIZONA BOARD OF REGENTS ON BEHALF OF THE UNIVERSITY OF ARIZONA, Tucson, AZ (US)

(72) Inventors: Samuel Barber, Tucson, AZ (US); Saurabh Jain, Tucson, AZ (US); Young-Jun Son, Tucson, AZ (US); Eugene Chang, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 664 days.

(21) Appl. No.: 17/048,962

(22) PCT Filed: Apr. 18, 2019

(86) PCT No.: PCT/US2019/028127
§ 371 (c)(1),
(2) Date: Oct. 19, 2020

(87) PCT Pub. No.: WO2019/204607
PCT Pub. Date: Oct. 24, 2019

(65) Prior Publication Data
US 2021/0241656 A1 Aug. 5, 2021

Related U.S. Application Data

(60) Provisional application No. 62/659,672, filed on Apr. 18, 2018, provisional application No. 62/659,680, (Continued)

(51) Int. Cl.
*G09B 23/28* (2006.01)
*A61B 17/24* (2006.01)
(Continued)

(52) U.S. Cl.
CPC .......... *G09B 23/285* (2013.01); *A61B 17/24* (2013.01); *A61B 34/10* (2016.02); *A61B 34/20* (2016.02);
(Continued)

(58) Field of Classification Search
CPC .......... G06F 30/00; G06F 3/011; G06F 3/012; G06F 3/016; G06F 3/0346; G09B 23/285;
(Continued)

(56) References Cited

U.S. PATENT DOCUMENTS 5,275,166 A 6/1994 Vaitekunas et al.

OTHER PUBLICATIONS

Favier, Valentin et al., "Geometric and Mechanical Evaluation of 3D-Printing Materials for Skull Base Anatomical Education and Endoscopic Surgery Simulation—A First Step to Create Reliable Customized Simulators", Dec. 18, 2017, Plos One. (Year: 2017).*
(Continued)

*Primary Examiner* — Cedric Johnson
(74) *Attorney, Agent, or Firm* — COZEN O'CONNOR (57) ABSTRACT

An apparatus has a device representing an endoscope, the device being either an endoscope or a dummy endoscope having shape and feel resembling an endoscope, and includes a tracker adapted to operate with a three-dimensional tracking system to track location and orientation of the device in three dimensions in a simulated operating-room environment. The apparatus also has a physical head model comprising hard and soft components, the device representing an endoscope configured to be inserted into the physical head model to provide a haptic feedback of endoscopic surgery.

13 Claims, 10 Drawing Sheets

Related U.S. Application Data filed on Apr. 18, 2018, provisional application No. 62/659,685, filed on Apr. 18, 2018.

(51) Int. Cl.

| | |
|---|---|
| *A61B 34/10* | (2016.01) |
| *A61B 34/20* | (2016.01) |
| *A61B 90/00* | (2016.01) |
| *B33Y 80/00* | (2015.01) |
| *G06F 3/01* | (2006.01) |
| *G06F 3/0346* | (2013.01) |
| *G06T 7/11* | (2017.01) |
| *G09B 23/30* | (2006.01) |
| *G16H 20/40* | (2018.01) |
| *G16H 40/63* | (2018.01) |
| *G16H 50/50* | (2018.01) |
| *A61B 17/00* | (2006.01) |
| *A61B 17/29* | (2006.01) |
| *A61B 17/32* | (2006.01) |
| *A61B 17/3201* | (2006.01) |
| *A61B 18/00* | (2006.01) |
| *A61B 18/14* | (2006.01) |
| *A61B 90/50* | (2016.01) |

(52) U.S. Cl.
CPC .............. *A61B 90/36* (2016.02); *B33Y 80/00* (2014.12); *G06F 3/011* (2013.01); *G06F 3/012* (2013.01); *G06F 3/016* (2013.01); *G06F 3/0346* (2013.01); *G06T 7/11* (2017.01); *G09B 23/30* (2013.01); *G16H 20/40* (2018.01); *G16H 40/63* (2018.01); *G16H 50/50* (2018.01); *A61B 2017/00119* (2013.01); *A61B 2017/00216* (2013.01); *A61B 2017/00707* (2013.01); *A61B 2017/00716* (2013.01); *A61B 17/29* (2013.01); *A61B 17/320016* (2013.01); *A61B 17/3201* (2013.01); *A61B 2018/00297* (2013.01); *A61B 18/14* (2013.01); *A61B 2034/101* (2016.02); *A61B 2034/105* (2016.02); *A61B 2034/107* (2016.02); *A61B 2090/365* (2016.02); *A61B 2090/372* (2016.02); *A61B 2090/502* (2016.02); *G06T 2207/10068* (2013.01); *G06T 2207/10072* (2013.01); *G06T 2207/30004* (2013.01)

(58) Field of Classification Search
CPC ......... G09B 23/30; A61B 34/10; A61B 34/20; A61B 90/36; A61B 2034/105; A61B 2034/107; A61B 17/24; A61B 17/29; A61B 17/320016; A61B 17/3201; A61B 18/14; A61B 2017/00119; A61B 2017/00216; A61B 2017/2017; A61B 2017/00707; A61B 2017/00716; A61B 2018/00297; A61B 2034/101; A61B 2090/365; A61B 2090/372; A61B 2090/502; B33Y 80/00; G06T 7/11; G06T 2207/10068; G06T 2207/10072; G06T 2207/30004; G16H 20/40; G16H 40/63; G16H 50/50

USPC .......................................................... 703/6
See application file for complete search history.

(56) References Cited

OTHER PUBLICATIONS

Chan, Harley H. L. et al., "Rapid Prototyping for Otolaryngology—Head and Neck Surgery: Applications in Image-Guidance, Surgical Simulation and Patient-Specific Modeling", Sep. 2, 2015, Plos One. (Year: 2015).*

Berens, Angelique Marie et al., "Computer-Aided Design and 3D Printing to Produce a Costal Cartilage Model for Simulation of Auricular Reconstruction", Sep. 27-30, 2015, AAO-HNSF Annual Meeting & OTO EXPO, American Academy of Otolaryngology—Head and Neck Surgery Foundation. (Year: 2015).*

Varshney, Rickul et al, "Development of the McGill Simulator for Endoscopic Sinus Surgery: A New High-Fidelity Virtual Reality Simulator for Endoscopic Sinus Surgery", Jul.-Aug. 2014, American Journal of Rhinology and Allergy, , OceanSide Publications, Inc. (Year: 2014).*

Carnegie, Shaun et al., "Endoscopic Neurosurgery Simulation: Implementation on the Evolution Engine", 2014, IEEE. (Year: 2014).*

Chan et al. (2015) "3D Rapid Prototyping for Otolaryngology—Head and Neck Surgery: Applications in Image-Guidance, Surgical Simulation and Patient-Specific Modeling", PLos One, Sep. 2, 2015, vol. 10, No. 9, e01366370.

Hoang et al. (2016) "Surgical Applications of Three-Dimensional Printing: A Review of the Current Literature & How to Get Started." Ann Transl Med., Nov. 24, 2016, vol. 4, No. 23, p. 456.

PCT/US19/28127 International Search Report and Written Opinion dated Jul. 1, 2019, 10 pp.

Varshney et al. (2014) "Development of the McGill Simulator for Endoscopic Sinus Surgery: A New High-Fidelity Virtual Reality Simulator for Endoscopic Sinus Surgery", Am J Rhinol Allergy, Jul.-Aug. 2014, vol. 28, No. 4, pp. 330-334.

PCT/US19/28131 International Preliminary Report on Patentability dated Aug. 5, 2019, 8 pp.

Khor et al. (2016) "Augmented and Virtual Reality in Surgery—the Digital Surgical Environment: Applications, Limitations and Legal Pitfalls." Ann. Transl. Med. Nov. 24, 2016, 10 pp.

Carnegie, S. et al., "Endoscopic Neurosurgery Simulation: Implementation on the Evolution Engine", IEEE, 1-2 (2014).

* cited by examiner

Body Tissue     Mucosa     Soft Tissue

Composite Mesh

FIG. 3B

FIG. 4A Angle-tipped forceps or biter

FIG. 4B Straight-tipped forceps or biter

FIG. 4C Angle-tipped scissors

FIG. 4D straight-tipped scissors

FIG. 4E straight-tipped electrocautery

FIG. 4F bent-tipped probe or cutter

FIG. 4G Clamp-on tracker

MIXED-REALITY ENDOSCOPE AND SURGICAL TOOLS WITH HAPTIC FEEDBACK FOR INTEGRATED VIRTUAL-REALITY VISUAL AND HAPTIC SURGICAL SIMULATION

RELATED APPLICATIONS

This application is a 35 U.S.C. § 371 filing of International Patent Application No. PCT/US19/028127, filed Apr. 18, 2019, which claims priority to U.S. Provisional Application Nos. 62/659,680, 62/659,685, and 62/659,672, all of which were filed on 18 Apr. 2018, the contents of which are hereby incorporated by reference in their entireties.

RELATED APPLICATIONS

The present document relates to co-filed applications entitled System for Integrated Virtual-Reality Visual and Haptic Surgical Simulator and System for Generating 3D Models for 3D Printing, and for Generating Video for an Integrated Virtual-Reality Visual and Haptic Surgical Simulator.

FIELD

The present document describes a training, practice, and enhanced operating environment for surgeons training for, performing, or teaching surgery. In particular, a training, practice, and performing tele- or virtual surgical environment is described for Functional Endoscopic Sinus Surgery (FESS). This document also highlights segmentation of critical structures, including the orbit, brain, cranial nerves, and vessels in augmented-reality and the training and practice environment includes visual, auditory, and haptic feedback.

BACKGROUND

Functional endoscopic sinus surgery (FESS) utilizes surgical endoscopes that allow visualization, magnification and lighting of structures in the sinuses and nose to perform minimally invasive surgery through the nose. The use of image-guided surgery provides the surgeon with intraoperative landmarks to avoid critical structures in the sinonasal cavity, with the goal of reducing complications into the orbit, brain, cerebrospinal fluid, or major vessels. Although these complications are rare, they can be catastrophic if they occur. FESS is commonly used in the surgical treatment of chronic sinusitis, the removal of sinonasal tumors, or in access to other craniofacial structures such as the orbital or cranial cavities.

FESS requires rigorous preoperative planning and careful intraoperative dissection of intricate anatomic structures. Due to each individual's unique anatomy, image-guided surgery is commonly used in complex cases, in which real-time 3-dimensional (3D) tracking systems determine positions of instruments relative to known skull base anatomy shown on visual displays. Although image-guided surgery has been shown to be helpful, several studies have shown that complication rates have not significantly decreased.

The endoscopes used in FESS are typically rigid endoscopes, providing image pickup from the surgical field from their distal end. Tools used in FESS are typically rigid, having a handle, long tubular or rod-shaped shafts, and operative devices at their distal end. These tools are inserted alongside, over, or under the endoscope; once inserted into the surgical field they are manipulated under visual observation from the endoscope until their distal end and operative devices are positioned as needed for the operation being performed. When inserting these tools, it is necessary to avoid undue pressure on, or damage to, structures within the nasal cavity that are not part of the surgical field—these structures are known to. Safe manipulation of these tools and endoscope through the obstacle course of turbinates and other structures within the nasal cavity and into the surgical field, and use of the tools to perform desired functions, requires practice.

SUMMARY

Our surgical simulation system is a mixed-reality surgical simulator with an immersive user experience that may, in some embodiments, incorporate patient-specific anatomy and may be used for preoperative planning and practice. The system includes a physical head model, a real or dummy endoscope which can be navigated, a tracking system configured to track location and angle of the endoscope with 6-degrees-of-freedom in virtual space, trackable instruments either real surgical instruments or dummy instruments modeled after real surgical instruments. In some embodiments, new surgical instruments or models thereof may be used. The tracking system also tracks virtual-reality goggles. A tracking, modeling, and display machine is configured to track a tip of the endoscope within the physical head model and identify corresponding locations in a CAD model of the physical head and to generate a video stream corresponding to a view of the CAD model from the corresponding location in the CAD model. This model allows for: 1) surgical simulation on patient-specific models in virtual reality, 2) the development of an operating room environment virtually, 3) the use of augmented-reality to highlight critical structures that can be highlighted through visual or auditory cues, 4) the recording of this virtual surgery on a patient-specific model to then be used as a tracer or guide for trainees performing live surgery on the specific patient.

In an embodiment, an apparatus has a device representing an endoscope, being either an endoscope or a dummy endoscope having shape and feel resembling an endoscope, having an attached tracker adapted to operate with a three-dimensional tracking system to track location and orientation of the device in three dimensions in a simulated operating-room environment. The apparatus also has a physical head model comprising hard and soft components, the device representing an endoscope is configured to be inserted into the physical head model to provide haptic feedback resembling that of using same or similar instruments and endoscopes in real endoscopic surgery.

DETAILED DESCRIPTION OF THE EMBODIMENTS

Our surgical simulation system is a mixed-reality surgical simulator with an immersive user experience that incorporates patient-specific anatomy.

Figure 1:
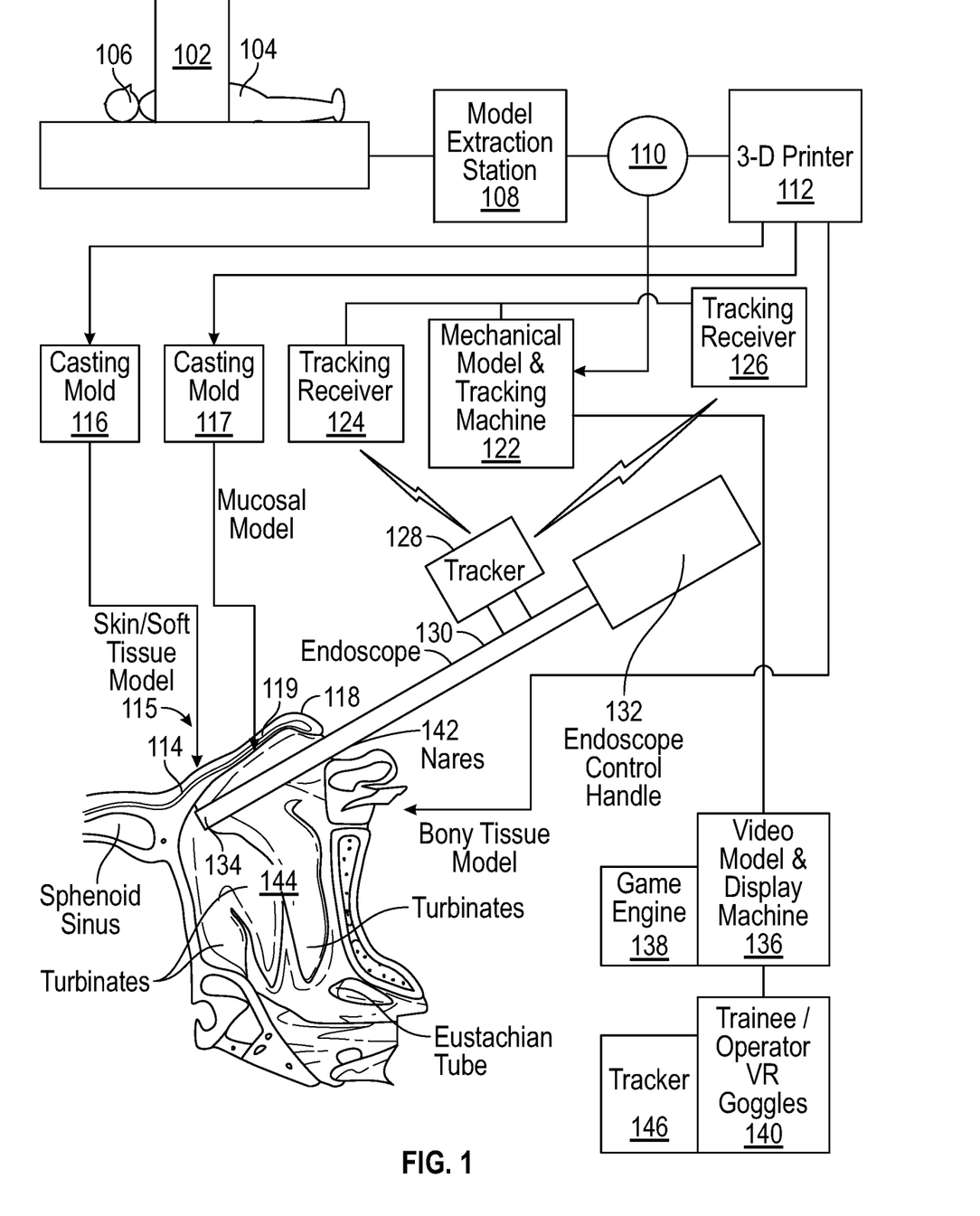
FIG. 1 is a block diagram of a system providing integrated virtual-reality and haptic feedback from an FESS endoscope to surgical trainees or to surgeons preparing for specific cases.
Figure 2A:
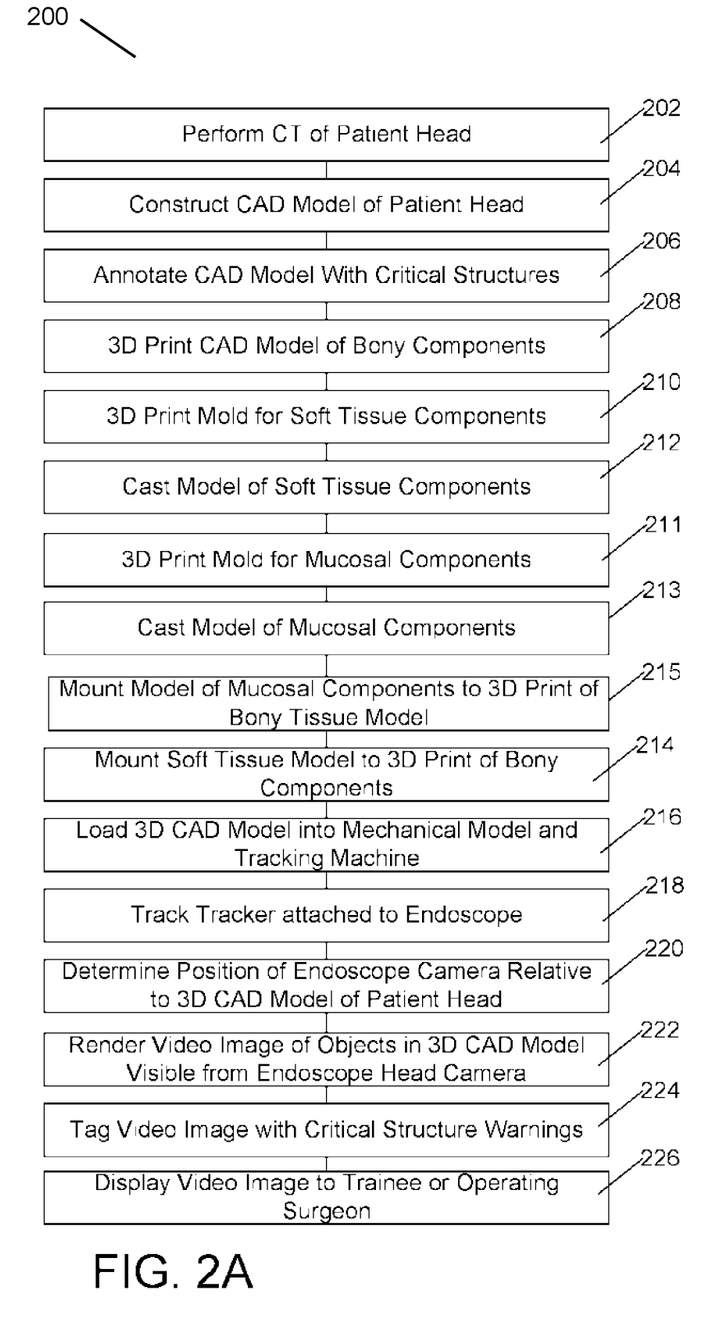
FIG. 2A is a flowchart of a method of training or surgical preparation using the system of FIG. 1.

In an embodiment, a method 200 (FIG. 2) of training or preparation for particular surgical cases begins with performing a computed tomography (CT) scan 202 using a CT scanner 102 (FIG. 1) to obtain three-dimensional radiographic imaging of the head 106 of a patient 104 in tomographic image stack form; in a particular embodiment the three-dimensional radiographic imaging of the head 106 includes a stack of tomographic slice images with 0.625-millimeter slices however other resolutions may be used. In an alternative embodiment, MRI imagers are used in place of CT scanner 102 to image the head and provide a similar stack of tomographic image slices, the stack of tomographic image slices being three-dimensional radiographic imaging.

In a particular embodiment, the CT scan or MRI three-dimensional radiographic imaging is of the head of a specific patient for which a surgeon wishes a simulated dry run before performing surgery. In alternative embodiments, the CT scan or MRI three-dimensional radiographic imaging is, in succession, a CT scan or MRI of a training series of increasing difficulty, including radiographic imaging of heads of patients for which FESS surgery has been performed; with this series a beginning trainee surgeon can have a series of VR and physical head models prepared with which to learn by practicing basic, moderate, and difficult surgeries.

Figure 2B:
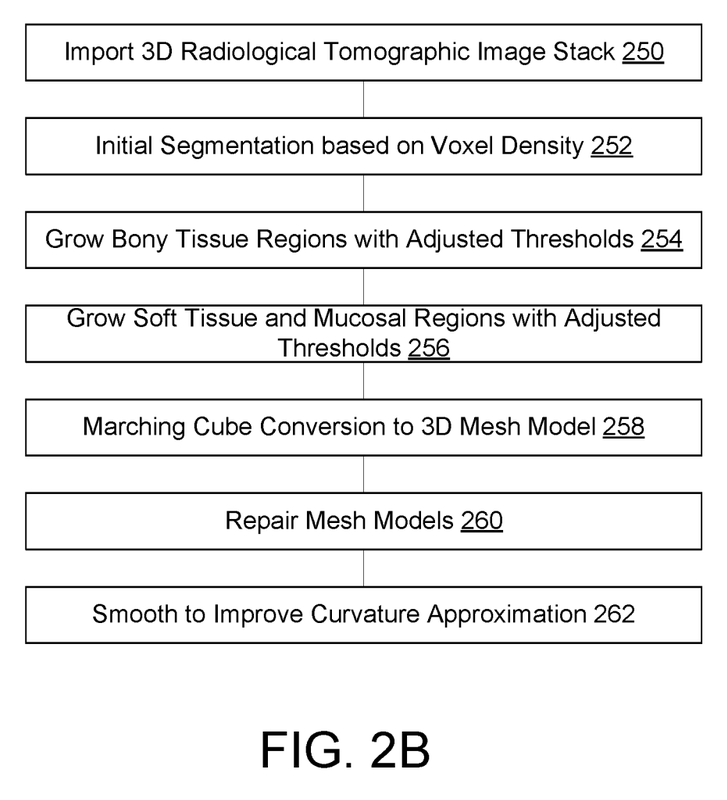
FIG. 2B is a detail flowchart of preparing CAD models of hard bony, mucosal, and soft tissues from tomographic radiological image stacks.
Figure 3:
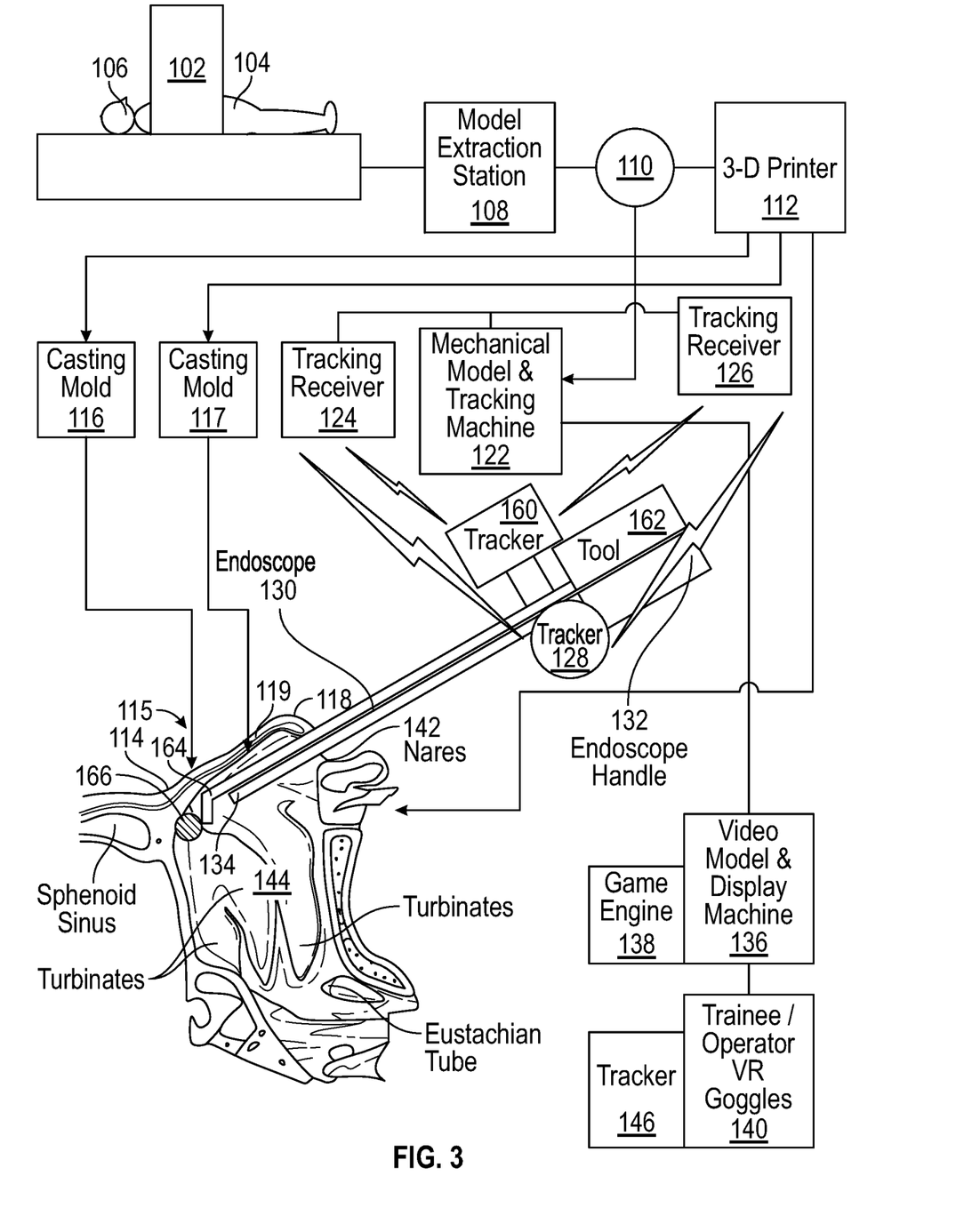
FIG. 3 is a block diagram of a system providing integrated virtual-reality and haptic feedback from an FESS endoscope and surgical tools to surgical trainees or to surgeons preparing for specific cases.
Figure 3A:
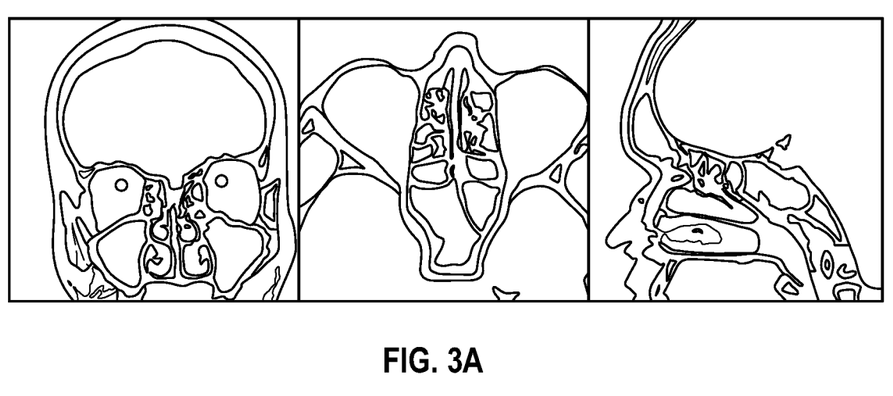
FIG. 3A is a schematic illustration of critical structures identified in the radiographic three-dimensional images.
Figure 3B:
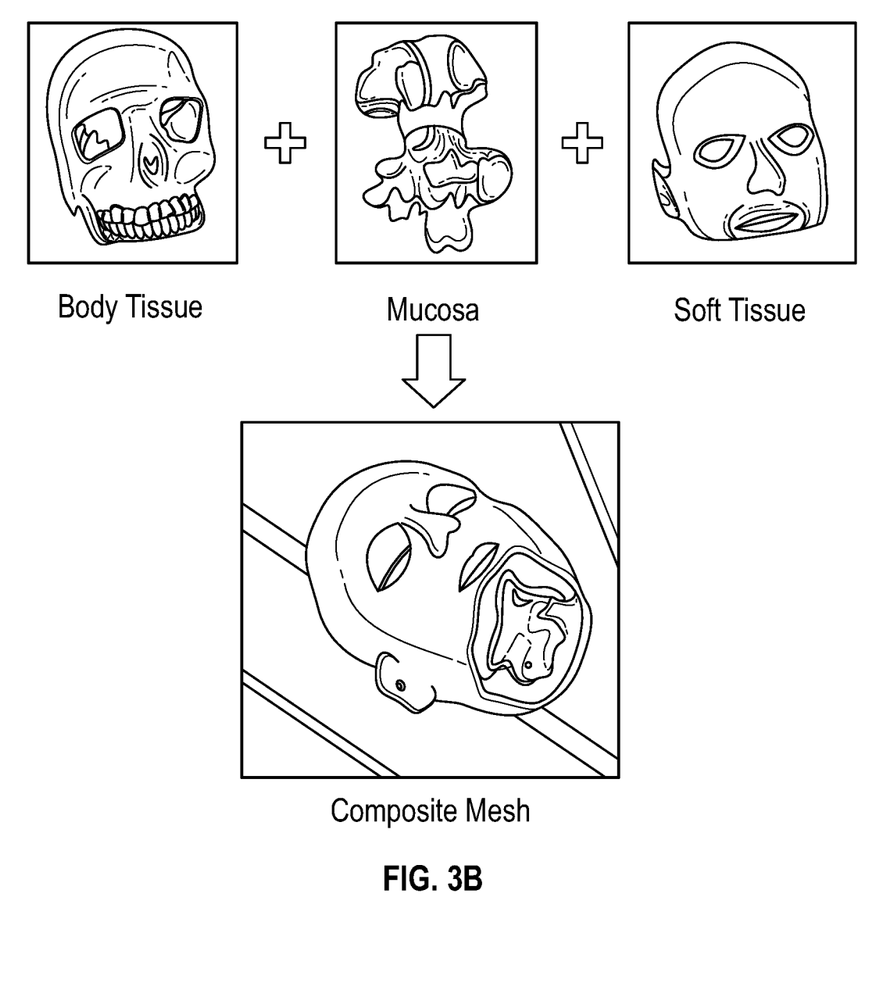
FIG. 3B is an illustration of bony, mucosa, and soft tissue portions of the computer-aided design (CAD) model of the head as replicated through 3D printing and assembled into the head physical model.

The three-dimensional radiographic imaging for a selected head is used to construct 204, on a model extraction workstation 108, a three-dimensional computer-aided design (CAD) model 110 of the head 106 of patient 104, the CAD model 110 includes in separate files a mesh model of the hard-bony structures of skull, and a mesh model of soft tissue structures including mucosa as well as the skin and septal cartilage of nose as illustrated in FIG. 3B. In an embodiment, after importing 250 (FIG. 2B) the three dimensional radiographic image stack into a voxel-based 3-D model, the hard bony structures and soft tissue, including the mucosa, are initially automatically segmented 252, being distinguished from each other based at least in part on voxel intensity, and in some embodiments initial segmentation is based on voxel intensity; CT typically shows greater X-ray absorption for calcified bony tissue than for soft tissue, while MRI images typically show less hydrogen for calcified bony tissue than for soft tissue, yet more hydrogen than for voids. Extracted or segmented imaged bony, mucosal, and soft tissue 3D voxel models are processed into mesh models of bony, mucosal and soft tissue structure; mesh model boundaries are generated with any inconsistencies (or holes) in the mesh models repaired to form CAD model 110.

Extracting and segmenting imaged bony and soft tissues into 3D mesh models is performed as illustrated in FIG. 2B. Segmentation of bony tissues into a bony tissue voxel model in an embodiment is done using a region growing method and threshold process 254, whereas for soft tissue and mucosa voxel models a semi-automatic region growing method is used 256; FastGrowCut and the segmentation module in 3-D Slicer functions are used for both the region growing and threshold process and the region growing methods. Skin, muscle, and other soft tissues are segmented from mucosal tissues based upon anatomic landmarks. A marching-cube surface-mesh reconstruction 258 is then performed on the voxel models to prepare a mesh model of each of the hard bony, mucosal, and soft tissues. Manual modification of the threshold and algorithm parameters on a regional basis may be done to avoid over-segmentation, under-segmentation and other artifacts, which may occur with volume averaging of bony and soft tissue densities in the head and neck.

The hard-bony tissue mesh model, mucosal tissue mesh model, and soft tissue mesh model from the marching cubes reconstructions are then repaired 260, first with a surface toolbox mesh-repair module of 3-D slicer (http://www.slicer.org), and further with Autodesk 3ds Max. In a particular embodiment, a Lapacian smoothing routine was used to revise mesh models to improve 262 the approximation of curvature without losing volume.

Both the hard-bony tissue and soft tissue portions of CAD model 110 are constructed in mesh form using the FastGrowCut Segmentation and Paint (with Editable intensity range for masking) modules in 3-D Slicer and repaired to eliminate holes with the 3D Slicer surface toolbox. The mesh models of CAD model 110 are further repaired using Autodesk 3ds Max to reduce the number of vertices for mesh optimization, and to prepare the model for 3D printing. The generated and repaired mesh models of hard bony tissue, soft tissue, and mucosal tissue form parts of CAD model 110 and are exportable in mesh form for use in 3D printers.

In embodiments, CAD model 110 is annotated 206 to build and tag to identify one or both of a model of a surgical target and models of critical structures at risk during FESS surgery or located near to the surgical target, as illustrated in FIG. 3B. Tagging may be in part manual and in embodiments may be in part automated using a classifier based on an appropriate machine-learning algorithm. The annotated critical structures may include one or more of the cranial nerves (CN) including the olfactory and optic nerves (CN-1, CN-2) together with the optic chiasma, anterior and posterior portions of the pituitary gland, the cranial nerves CN-3, CN4, and CN6 that innervate the orbital muscles, and the cribriform plate. The critical structures tagged may also include blood vessels such as the anterior ethmoidal artery, and internal carotid artery that can be at risk during endoscopic surgeries performed through the nares. The critical structures are identified based upon known anatomic landmarks visible in the three-dimensional radiological imaging.

In an embodiment, during segmentation soft tissue is identified, including mucosa lining the nasal cavity and paranasal sinuses including the inferior, middle, and superior turbinates, maxillary sinuses, anterior ethmoid sinuses, agger nasi, ethmoid bullae, posterior ethmoid sinuses, sphenoid sinus, and frontal sinus.

Neural and arterial structures at risk for damage during surgery were identified and segmented separately, these are tagged as critical structures so that alarms can be sounded when a virtual surgical tool enters or touches them. These included the anterior ethmoidal artery, internal carotid artery, and cranial nerve II also known as the optic nerve and chiasm. Surface meshes were generated within 3-D Slicer, and exported in wavefront (OBJ) format.

Further, hard tissue is identified based on voxel density including the bone lining the medial orbit known as the lamina papyracea. Bony structures of the skull identified in this embodiment include the Mandible, Maxilla, Sphenoid, Ethmoid, Frontal, and Temporal Bones.

Skin & muscle soft tissues are separated from mucosa based on known anatomic landmarks.

The bony structures of CAD model 110 are then replicated 208 on a 3D printer 112 to prepare a hard-plastic physical model 114 of those hard-bony structures. In an embodiment, a stereolithographic (SLS) 3-D printer based upon photopolymerization of liquid resin is used to prepare hard plastic physical model 114. In a particular embodiment, a Formlabs Form2 (trademark of Formlabs, Inc., Somerville, Massachusetts) was used to prepare hard plastic physical model 114 of hard bony parts as defined in CAD model 110. In an alternative embodiment, a fused deposition (FDM) 3D printer, such as a Creality Ender 3 (trademark of Shenzhen Creality 3D Technology Co., Ltd, Shenzhen, China) or a Zcorp 650 (3D Systems, Rock Hill, South 27 Carolina). was used to prepare hard plastic physical model 114 from polylactic acid (PLA) filament, in other alternative embodiments hard plastic physical model 114 may be prepared with an FDM printer using extrudable Nylon or polyethylene terephthalate filament using a dual-extruder printer with polystyrene (HIPS) temporary supporting structures.

3D printer 112 is also used to prepare 210, by 3D printing, a casting mold 116 configured for casting 212 a soft silicone model 118 of selected soft tissue structures, including skin and septal cartilage of nose, as described in CAD model 110. In an embodiment, a mold is directly printed. In an alternative embodiment, a rigid model of the selected soft tissue structures is printed, this being then used as a form to cast a flexible silicone mold that is in turn used to cast soft silicone model 118 of soft tissue structures. In an alternative embodiment, soft silicone model 118 is directly printed using a flexible UV-polymerizable resin in an SLA printer such as the Form2 printer 3D printer 112 is also used to prepare 211 a casting mold 117 configured for casting 213 a soft silicone model 119 of selected mucosal structures, such as line the interior of nasal cavity and sinuses, as described in CAD model 110. Once cast 213, the soft silicone mucosal model 119 is mounted 215 to the hard-plastic physical model 114. In an alternative embodiment, model 119 of mucosal structures has been directly 3D printed using an SLS-type 3D printer such as a Form2 printer and flexible, UV-curable, resin.

With reference to FIG. 3B, once the soft silicone model 118 of soft tissue structures is cast, 212, and after mounting 215 the mucosal model 119 to the hard plastic bony tissue model, the soft silicone model 118 of soft tissue structures is mounted 214 to the hard plastic physical model 114 of bony tissues to create the head physical model 115, the head physical model 115 including hard plastic physical model 114, soft silicone model 119 of mucosal structures, and soft silicone model 118 of soft tissue structures.

Figure 6:
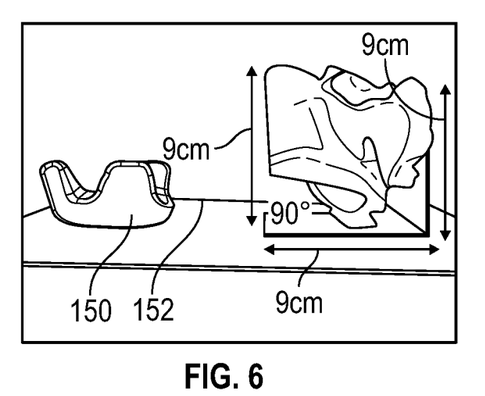
FIG. 6 is a photograph illustrating a hard-plastic physical model representing bone attached to a tracker to permit easy relative movement analysis between the physical model and the endoscope tip.
Figure 7:
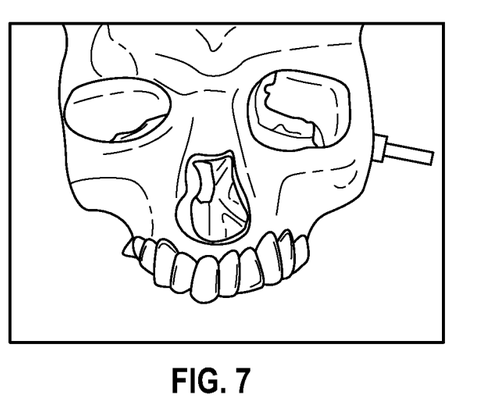
FIG. 7 is a top view photograph of the hard-plastic physical model representing bone.
Figure 8:
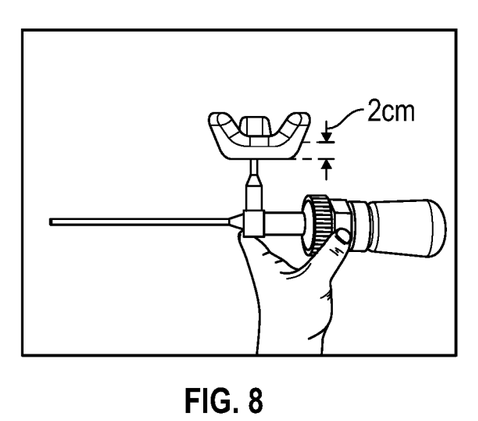
FIG. 8 is a photographic view of a tracker attached to a dummy endoscope.

CAD model 110 is also loaded 216 into a mechanical modeling and tracking machine 122 equipped with tracking receivers 124, 126. Tracking receivers 124, 126 are configured to track 218 location and orientation in three-dimensional space of a tracker 128 that is attached to a dummy endoscope 130, in a particular embodiment, tracking receivers 124, 126 and tracker 128 are HTC Vive (HTC, New Taipei City, Taiwan) trackers and the virtual reality goggles are an HTC Vive headset; other virtual reality goggles and trackers may be used. In an embodiment, head physical model 115 is at a known location, in other embodiments, hard plastic physical model 114 is attached to another tracker 150 through a short steel rod 152 as illustrated in FIG. 6. Also attached to dummy endoscope 130 is endoscope handle 132 that may include operative controls. In a particular embodiment, operative controls on endoscope handle 132 include camera angle selection buttons. In an alternative embodiment, a real endoscope may be used in place of the dummy endoscope. For purposes of this document, a device representing an endoscope may be either a dummy endoscope or a real endoscope.

The mechanical modeling and tracking machine 122 then uses the location and orientation of the tracker 128 on the endoscope 130 to determine 220 a location and orientation of endoscope head 134 in the head physical model, which is in turn aligned and registered to a virtual head as modeled by CAD model 110 executing on modeling and tracking machine 122, the CAD model 110 being derived from the 3D image stack determined from MRI or CT scans. Since the head physical model is registered to the CAD model 110, each location of endoscope head 134 in the head physical model corresponds to a location in the CAD model 110.

Interaction of the device representing an endoscope with the head physical model as the device is inserted into the model provides tactile or haptic feedback to a surgeon or trainee that resembles tactile or haptic feedback as the surgeon or trainee inserts a real endoscope into a patient's real head.

An endoscope alone, however, is useful to visually inspect internal surfaces within the nasal cavity but cannot by itself perform FESS surgery. To perform surgery, additional surgical tools are inserted into a patient's head along with the endoscope.

To provide simulated tactile or haptic feedback to a surgeon or surgical trainee of manipulation of surgical tools in a head as well as feedback of manipulating the endoscope, in embodiments one or more devices resembling surgical tools are provided (FIG. 4). These tools may include any combination of an angle-tipped forceps or biter 460 illustrated in FIG. 4A, a straight-tipped forceps or biter 462 FIG. 4B, an angled-tipped scissors 464 FIG. 4C, a straight-tipped scissors 466 FIG. 4D, a straight-tipped electrocautery 468 FIG. 4E, a bent-tipped probe or alternatively a bent-tipped cutter 470 FIG. 4F, a bent-tipped electrocautery (not shown), a bent-tipped or straight-tipped drills (not shown), straight or bent suction tubes (not shown), microdebriders (not shown), straight tipped probes and cutters (not shown), and other tools as known in the art of FESS surgery; the tool may in an embodiment be a new or experimental tool of unique shape. Each device resembling surgical tools may be a 3-D print of a tool with an embedded 3-D tracker 402, 404, 406, 408, 410, 412, or may be a real surgical tool with a clamp-on 3-D tracker as illustrated in FIG. 4G. The clamp-on 3-D tracker has a 3-D tracking device 420 and clamp 422 and is configured to mount with a setscrew 424 to a shaft or body 426 of a surgical tool or 3-D model of a tool. Each tool has a corresponding 3D mesh model used in the gaming engine of the modeling and display machine to track position of the tool tip and to derive an image of the tool tip when the tool tip is in a field of view of the simulated endoscope tip. In an embodiment, the devices resembling surgical tools may be equipped with short-range radio-activated vibrators to provide haptic feedback resembling that of an operating drill or to provide alarms generated when tool tips approach critical structures.

Figure 4A:
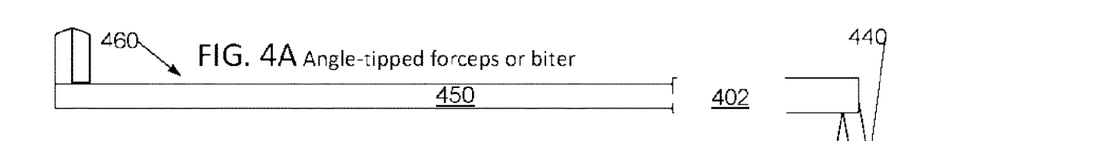
FIG. 4A-4F illustrate of tracker-equipped tools such as may be used with the endoscope. These include FIG. 4A illustrating an angle-tipped forceps or biter, FIG. 4B illustrating a straight-tipped forceps or biter, FIG. 4C illustrating an angled-tipped scissors, FIG. 4D illustrating a straight-tipped scissors, FIG. 4E illustrating a straight-tipped electrocautery, FIG. 4F illustrating a bent-tipped probe or alternatively a bent-tipped cutter.
Figure 4B:
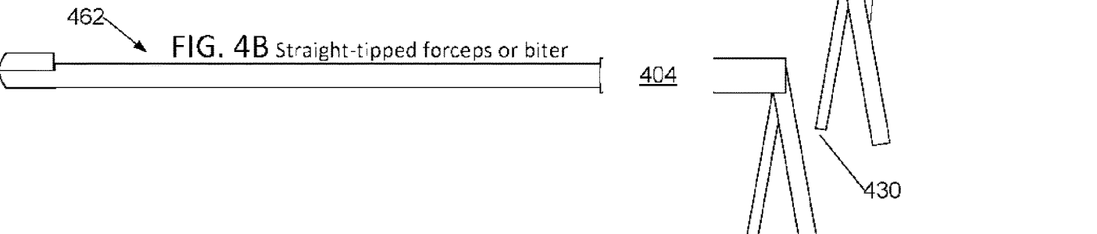
Figure 4C:
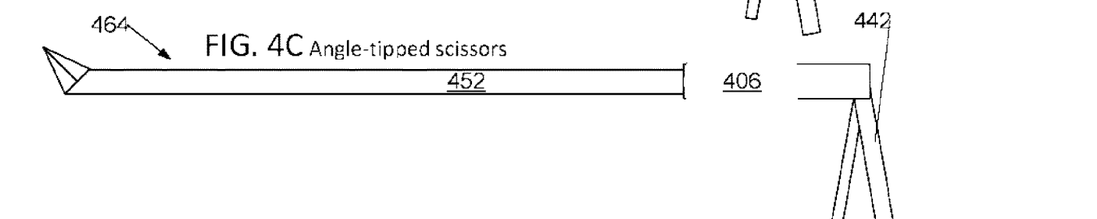
Figures 4D, 4E:
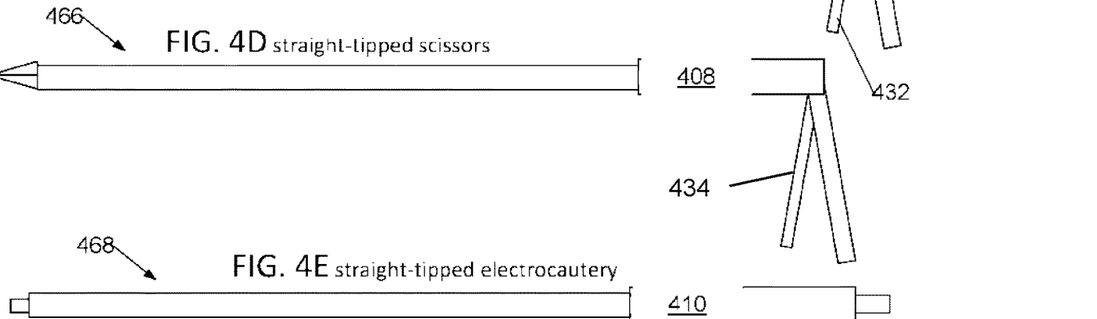
Figure 4F:
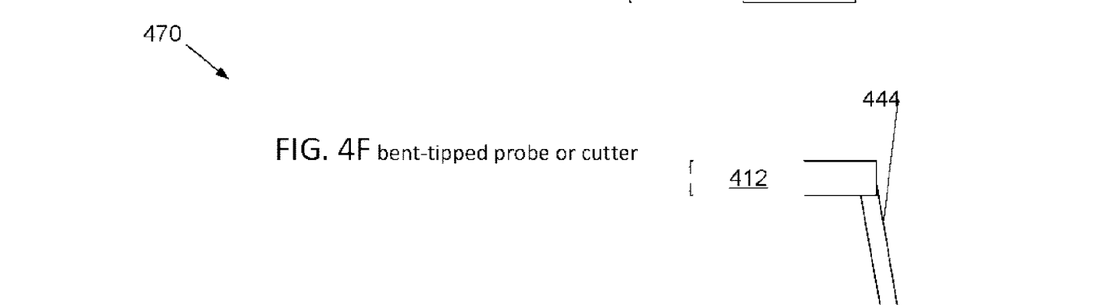

Tools used in FESS, such as forceps, biters, and scissors, often have a long, narrow, shaft 450, 452 configured to fit through the nares into the nasal cavity, they also have a handle 440, 442, 444 that allows the user to control their angle of orientation within the nasal cavity. These tools operate when an operating lever 430, 432, 434 is pressed, the operating lever being coupled through an operating rod that is typically disposed within the shaft 450, 452. Simple cutters and probes, as illustrated in FIG. 4F, do, however, lack an operating lever. For increased realism, operating levers of devices resembling a surgical tool may be instrumented with sensors configured to sense pressure on the operating lever, and transmit sensed pressure to the video modeling and display machine 136.

Figure 4G:
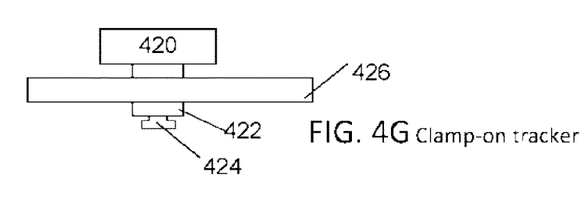
FIG. 4G illustrates a clamp-on tracker attachment that may be attached to a 3D printed model of a surgical tool, or to a real surgical tool, to track the tool in real time.

FIG. 4G illustrates a clamp-on tracker attachment that may be attached to a 3D printed model of a surgical tool, or to a real surgical tool, to track the tool in real time.

A computer model of each tracker-equipped surgical tool 460, 462, 464, 466, 468, 470 is incorporated into the mechanical model and tracking machine 122 and video model and display machine 136. The mechanical model and tracking machine 122 uses information received through multiple tracking receivers 124, 126 to determine position and orientation of both the tracker 128 on the endoscope 130 (FIG. 3) and tracker 160 on the tracker-equipped tool 162 to determine position and orientation of the tip 134 of the endoscope and operating portion 164 of the tool.

Meanwhile, a video modeling and display machine 136 executes a video game engine, in an embodiment the video game engine is the Unity Game Engine, in a particular embodiment Unity Engine V2017.3, (Trademark of Unity Technologies, San Francisco, California) was used, the video modeling and display machine 136 also executes the CAD model 110 of the head. Together the mechanical modeling and tracking machine and video modeling and display machine form a tracking, modeling, and display machine. In an alternative embodiment, modeling and tracking machine 122 and video modeling and display machine 136 are combined within a single tracking, modeling, and display machine executing a plurality of modules.

Video modeling and display machine 136 executing a video gaming engine 138 determines objects represented in CAD model 110 that are in view of the endoscope head 134, including anatomy of the head, at one of three selectable endoscope viewing angles, and renders 222 the objects in view of the endoscope head 134 into a video image. The objects represented in CAD model 110 may include models of foreign objects or tumors 166 upon which surgery is to be conducted. The gaming engine 138 also determines whether a tip 164 of any device resembling a surgical tool 162 is in a field of view of the endoscope as oriented, and renders that into the video image. In an embodiment the game engine is the Unity Game Engine v2017.3 (Unity Technologies). The present system is adapted to render objects in view of straight as well as angled endoscopes with accurate field of view. The game engine includes capability of photo-realistic rendering in real-time with dynamic lighting sources and shadows, in an embodiment the dynamic lighting source is chosen to correspond to a lighting fiber of a real endoscope so rendered images strongly resemble images seen through an endoscope camera during live surgeries. This video image represents a view corresponding to a view through an endoscope at a corresponding position in the patient's head 106. The video image corresponding to a view through the endoscope tip may then be tagged 224 with indications of critical structures and presented 226 to a trainee or operating surgeon through virtual reality goggles 140 as if on an endoscope monitor with images of other objects in a virtual operating room. Virtual reality goggles 140 are also equipped with a tracker 146.

Mechanical modeling and tracking machine 122 compares computed locations of both the endoscope tip 134 and tool tip 164 to locations of critical structures as flagged in model 110, and provides alerts when either tip 134, 164 is positioned to damage those critical structures. These critical structures include the orbits, cribriform plate, cavernous sinus, and multiple cranial fossae of the skull; when the video model and game machine 136 detects entry of a simulated surgical tool tip into or against one of these critical structures, the video model and game machine sounds an audible alarm or displays a visual alarm; in some embodiments a vibrator is used to provide a haptic alarm. In an alternative embodiment, alarms are generated upon a simulated surgical tool tip approaching one of these critical structures that have been tagged in the mucosal mesh model.

The system includes, within video model and game machine 136, a virtual reality model of a virtual operating room, including 3-D models of much common operating-room equipment such as an operating table, instrument tray, electrocautery machine, endoscope illuminator/camera controller, and endoscope monitor.

Figure 5A:
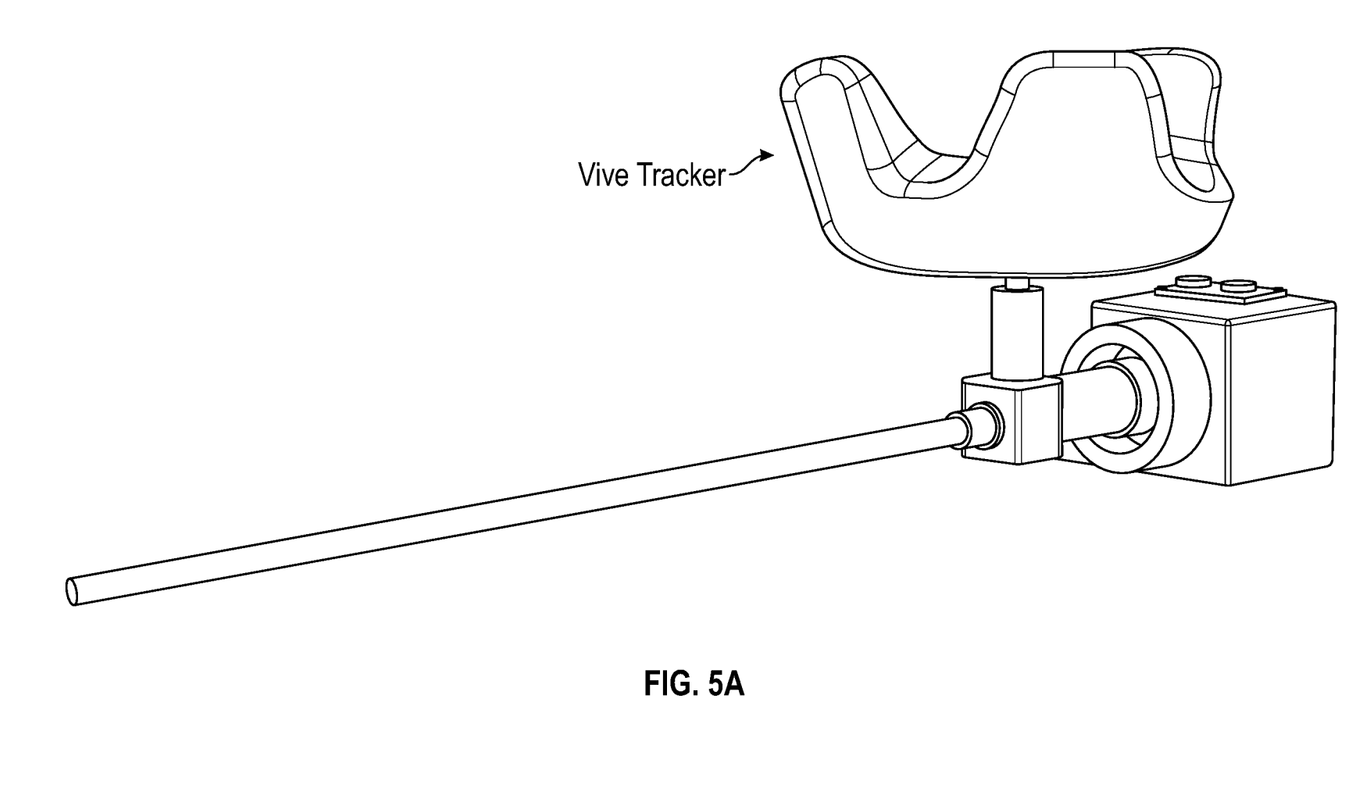
FIG. 5A is a photograph illustrating a tracker attached to an endoscope.
Figure 5B:
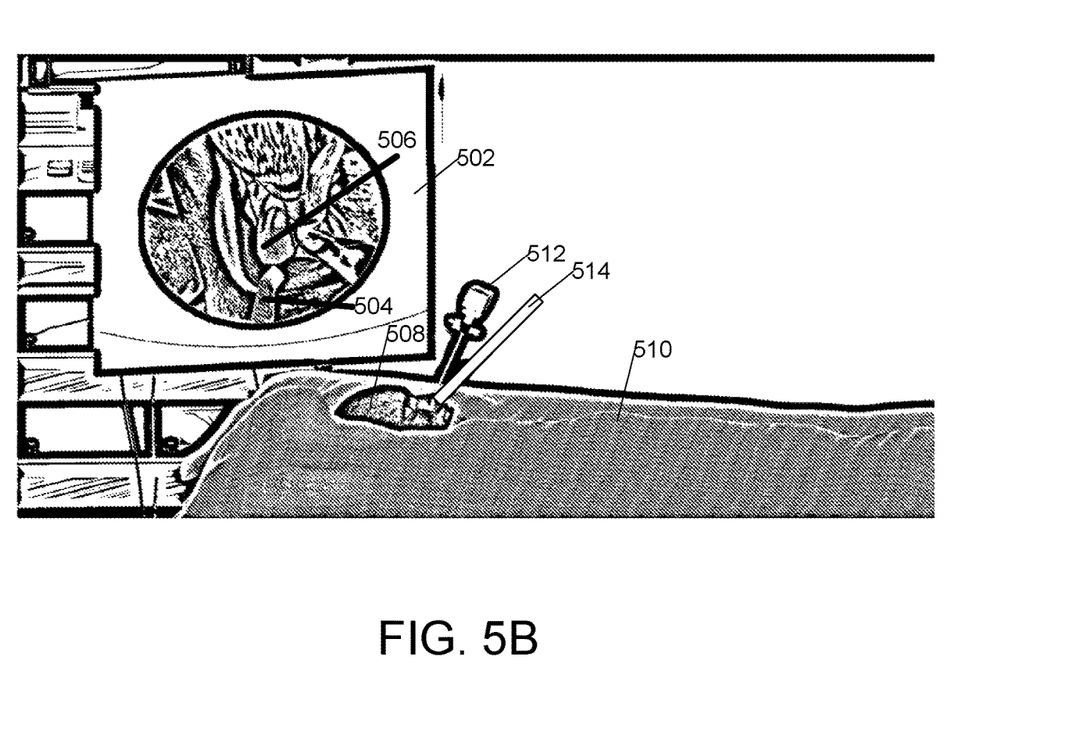
FIG. 5B illustrates a virtual-reality operating room environment, with draped patient, endoscope and surgical tool, and endoscopic monitor.

In operation, a trainee or operating surgeon puts on virtual reality goggles 140 then picks up and manipulates the endoscope 130 to insert endoscope head 134 into nares 142 of head physical model 115 into nasal cavity 144 of head physical model 115; the trainee or surgeon may also insert one or more tools 162 through the nares 142 into nasal cavity 144. While the surgeon is inserting the endoscope and tools, tracker 146 tracks location and angle of virtual reality goggles 140 to permit synthesis in video model and game machine 136 of a video stream incorporating a view of the virtual operating room with a virtual patient having head aligned and registered with a physical location of physical head model 115, and draped as typical for FESS surgery. In an embodiment, the view of the virtual operating room includes an image of an endoscope aligned and positioned according to tracked position and orientation of endoscope 130. The virtual operating room includes a virtual operating room monitor providing the virtual reality rendered video image as viewed from the endoscope tip, potentially including an image of the surgical tool tip 504 as well as an image of tumor to be resected 506, permitting the trainee or operating surgeon to view the rendered video image by aiming his or her head, and virtual reality goggles 140, at the virtual operating room monitor 502, as illustrated in FIG. 5B. Also visible in the VR goggle display may be, depending on VR goggle position and orientation, the simulated head 508 of properly draped patient 510, endoscope 512, and surgical tool 514

In an embodiment, the tracking and modeling machine 122 tracks position of the endoscope head 134 in physical model 115 and provides alerts when endoscope head 134 approaches locations corresponding to tagged critical structures in CAD model 110. In an embodiment these alerts are provided as aural alerts and as visual alerts by superimposing warnings and images of critical structures on the virtual endoscope images presented on the virtual operating room monitor thereby simulating an alternative embodiment that presents visual warnings on actual endoscope images during live surgeries.

While the trainee or surgeon manipulates the endoscope and surgical tool or tools, mechanical interactions of endoscope 130 and endoscope head 134 with the head physical model 115 provide tactile, or haptic, feedback to the trainee or operating surgeon, the tactile feedback greatly resembling tactile feedback felt during actual surgeries on sinuses, pituitary, and other organs accessible to endoscope 130 through nares 142. Tactile and haptic feedback is inherent to using 3D printed dummy endoscopes and other tools in the shape of real surgical tools, and having a trackable patient skull with anatomic features with which the endoscope and other surgical tools physically interact. One aspect of tactile feedback is the feel of the endoscope and its controller, and when present the surgical tools, in the trainee's hands each with 6 full degrees of freedom, providing a proprioceptively authentic feel in a room-scale immersive virtual-reality environment.

In embodiments, dummy endoscopes and dummy surgical tools are 3D printed with FDM printers.

In an alternative embodiment tactile feedback is enhanced with a vibratory mechanism within the dummy endoscope or other dummy tools to simulate a surgical drill, suction probe or suction cautery such as may be used during actual surgeries.

Similarly, the virtual reality rendered video image presented on the virtual operating room monitor with virtual reality goggles 140 provides visual feedback like visual images seen by a trainee or operating surgeon while performing similar operations. The position and angle of the VR goggles are tracked and the simulated OR environment is displayed through the VR goggle with position and size of the simulated endoscope monitor dependent on angle and position of the VR goggle. In this way, movement of the trainee or operating surgeon's head provides realistic movement of stationary objects in his field of view like the simulated endoscope monitor while he is wearing the VR goggles. Both the head physical model 115 and virtual reality rendered video based on CAD model 110 are patient-specific since CAD model 110 is derived from the three-dimensional radiographic images of a specific patient's head 106.

In an embodiment, dummy endoscope 130 has a lumen and operative tools can be inserted through that lumen, in particular embodiments these tools may include drills for penetrating through bone into sinuses or through bone to reach a pituitary gland; these tools can also penetrate through hard plastic of physical model 114 during practice procedures.

Figure 9:
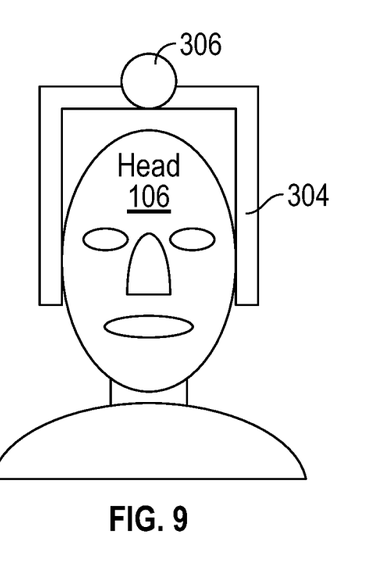
FIG. 9 is a schematic sketch illustrating a tracker attached through a frame to a patient's head.

In an alternative embodiment, for use in live surgeries, a frame 304 is attached to the patient's head 106, and a tracker 306 is positioned on the frame. The patient's head is registered to the tracking system with the CAD model 110 aligned to the patient's head 106. In this embodiment, the tracking and modeling machine 122 tracks position of the endoscope head and provides alerts when tracked endoscope head 134 approaches tagged critical structures as identified in the CAD model 110, in an embodiment these alerts are provided as aural alerts and as visual alerts by superimposing warnings and images of critical structures on images obtained through an endoscope camera viewing the patient's nasal cavity and sinuses from endoscope head 134.

Figure 10:
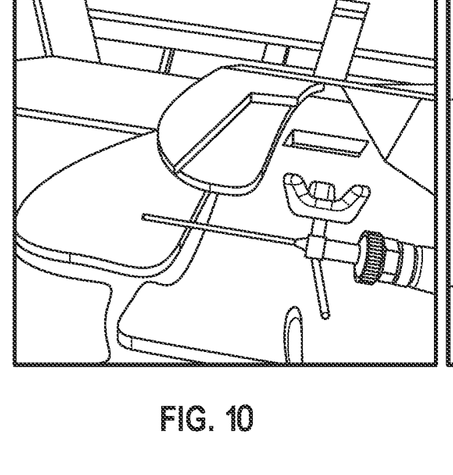
FIG. 10 is an illustration of a rendered virtual reality view of the CAD model of the head with superimposed images of specific critical structures.
Figure 11:
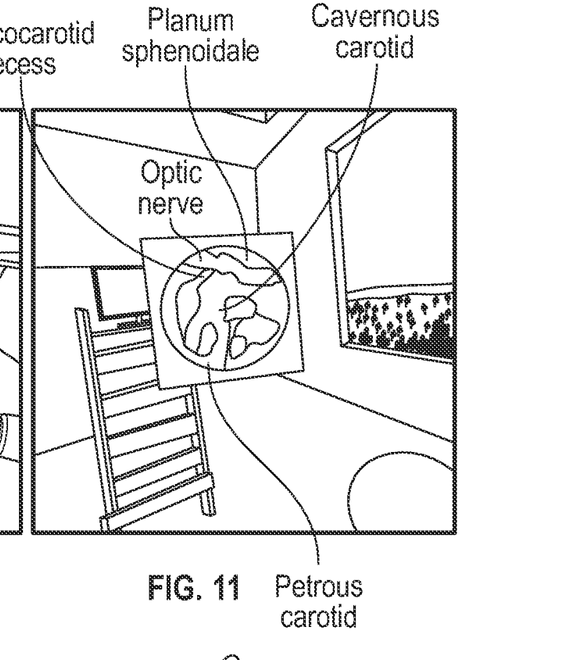
FIG. 11 is an illustration of a rendered virtual reality endoscopic view as seen from an end of the endoscope with critical structures highlighted.
Figure 12:
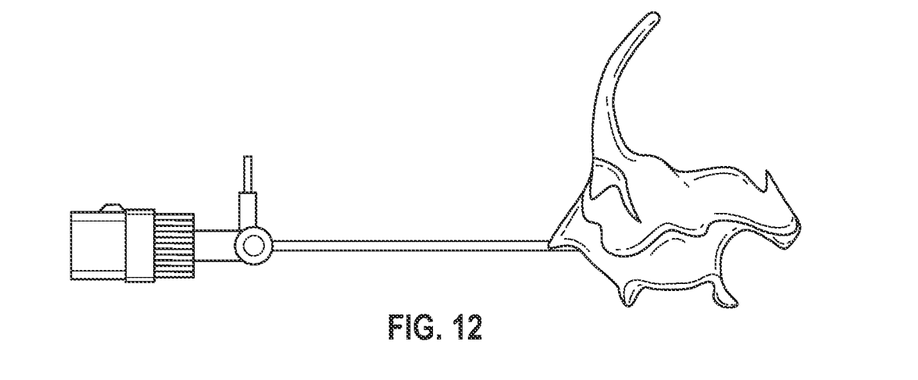
FIGS. 12 and 13 illustrate in full and cutaway views an endoscope inserted into nasal cavities of a physical model of the head, the physical model having both soft silicone and hard plastic components.
Figure 13:
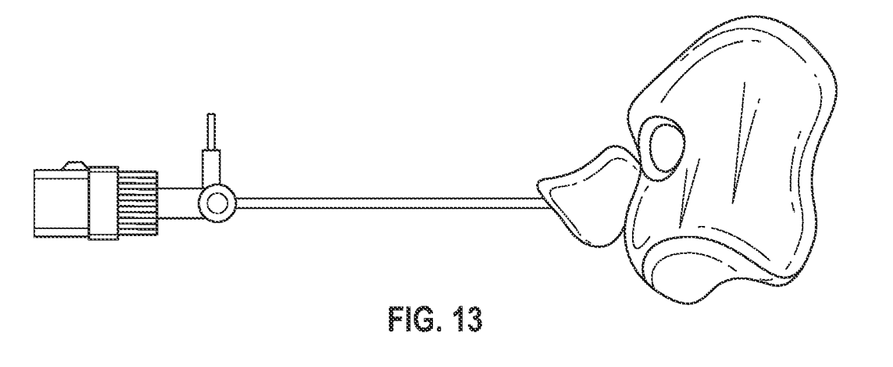

In an alternative embodiment, critical structures may be highlighted and displayed as illustrated in FIG. 10 as structures shown with reference to the head and FIG. 11 as highlighted structures in an endoscope view. FIG. 10 illustrates critical structures viewed in projection superimposed on the CAD model 110.

In an alternative embodiment, the entire motion of the endoscope and operative tools is recorded by the operating surgeon and then transmitted to another site to provide a tracing of the surgery to be then mirrored by a second surgeon performing live surgery (tele-surgery), or repeated by trainees to provide repetitive guided training.

In an alternative embodiment, positions of head physical model or patient head, and endoscope as detected by the trackers are recorded throughout a practice or real surgical procedure. In an embodiment, a score is produced based on time to perform a predetermined task with penalties applied for approach of simulated tool tip to simulated critical structures; in embodiments motion tracking of tool and endoscope is used to determine economy of movement and the score is also based on economy of movement. In a particular embodiment, a machine-learning procedure is trained on beginning and experienced surgeons and motion tracking to provide personalized feedback to trainee surgeons and score users on their relative level in performing surgery. This feedback could be used to advance users from a beginner to expert level, or evaluate the level of surgeons in the community. Relative motions of endoscope and instrument to head as recorded are then analyzed using the 3D CAD model and critical structures tagged in the CAD model to provide feedback to the trainee surgeon. Such analysis may include indications of safer or faster ways the procedure could be performed, or be used to evaluate surgeons already performing surgery. For purposes of this document, derivation of the score and its use in training surgeons by giving real-time feedback to users, either by altering the level of difficulty of the simulation, providing visual/auditory/haptic feedback and cues to assist in surgery, and provide objective feedback or score on the simulation is known as the virtual coach. This could be used to evaluate proficiency during training, as well as provide a method of continued certification for practicing surgeons.

In an alternate embodiment, trackers are coupled to a real endoscope and real surgical tools, and a tracker on a frame is clamped to the same patient's head as used to generate the CT or MRI radiological tomographic image stack from which the CAD model was derived. The physical head model is not used in this alternate embodiment, the CAD model is registered to the patient's head. The modeling and display machine tracks locations of the endoscope and surgical tools tips in the CAD model—corresponding to positions in the patient's head—and generates visual or aural alarms when these tips approach critical structures tagged in the CAD model. These alarms serve to assist surgeons in avoiding damage to those critical structures.

For purposes of this document, the term "resilient polymer" shall include rubberlike polymeric materials, including polymerized Fromlabs elastic resin, resilient silicones and some soft carbon-based synthetic rubbers and flexible plastics like molded latex and sorbothane, adapted to being formed into flexible reproductions of human soft tissue such as skin and muscle and having Shore-A hardness no greater than 85. The term "hard plastic" shall include polymeric materials significantly harder than resilient polymers as defined above, including most acrylonitrile butadiene styrene (ABS), high impact polystyrene (HIPS), and polylactic acid (PLA) 3D printer filaments, and polymerized Formlabs standard-hardness grey resin.

Experimentally, Vive trackers were reliably tracked by Vive lighthouse base stations to less than a centimeter, updating the position of the tools and user in the virtual environment without detectable latency. The endoscope could register correctly the modeled danger-zones with audio and visual cues time-synchronously. This framework provides a cost-effective methodology for high-fidelity surgical training simulation with haptic feedback. Through virtual simulation, personalized training programs could be developed for trainees that are adaptive and scalable on any range of difficulty and complexity. Proposed approaches to VR can be extended to the telemedicine world, in which surgeons operating in remote locations can be assisted by the experts aiding from tertiary care centers. State-of-the-art surgical navigation systems such as the system herein described provide reliable optical and electromagnetic-based tracking with accuracy within potentially 2 mm. These navigation workstations confirm anatomic location but do not reduce the risk of surgical complications down to 0%. Additional features from our technology could be translatable to develop AR-based navigation, which can further improve safety in the operating room.

Combinations of Features

The features herein described may be combined into a functional surgical simulation system and environment in many ways. Among ways anticipated by the inventors that these features can be combined in various embodiments are:

A multimode VR apparatus designated A including an endoscope device adapted to represent an endoscope, the endoscope device selected from an endoscope and a dummy endoscope having shape and feel resembling that of an endoscope; a wireless tracker adapted to operate with a three-dimensional tracking system to track location and orientation of the endoscope device in three dimensions in a simulated operating room environment; and a video modeling and display machine configured with a computer-aided design (CAD) model of a head and adapted to provide a simulated head environment, providing a simulated endoscope view. The apparatus also includes a physical head model comprising hard and soft physical components, the endoscope device being configured to be inserted into the physical head model to provide a tactile representation of manipulation of an endoscope in a head to a person handling the endo-scope device.

An apparatus designated AA including the multimode VR apparatus designated A wherein the video modeling and display machine comprises a gaming engine adapted simulate endoscope view of the simulated head environment An apparatus designated AB including the apparatus designated A or AA wherein the physical head model comprises a wireless tracker, and where the computer-aided design (CAD) model of a head is registered to a tracked position of the physical head model.

An apparatus designated AC including the apparatus designated A, AA, or AB wherein the physical head model comprises a hard-plastic portion prepared by 3D printing representative of bony tissue and a resilient polymer portion representative of skin.

An apparatus designated AD including the apparatus designated A, AA, AB or AC and including a surgical tool device having shape and feel resembling that of a surgical tool adapted for functional endoscopic sinus surgery (FESS) selected from the group consisting of forceps, biting forceps, scissors, a probe, and an electrocautery, the tool device further comprising a wireless tracker adapted to operate with the three-dimensional tracking system to track location and orientation of the tool device in three dimensions in the simulated head environment.

An apparatus designated AE including the apparatus designated AD wherein the simulated endoscope view includes a simulated view of the tool device.

An apparatus designated AF including the apparatus designated A, AA, AB, AC, AD or AE wherein the video modeling and display machine is further configured to provide a simulated operating room (OR) environment with the simulated endoscope view displayed on a simulated endoscope monitor.

An apparatus designated AFA including the apparatus designated A, AA, AB, AC, AD, AE, or AF wherein the tool device resembles a surgical tool selected from the group consisting of forceps, biting forceps, scissors, a probe, a drill, and an electrocautery.

An apparatus designated AG including the apparatus designated A, AA, AB, AC, AD, AE, or AF further including a virtual-reality (VR) goggle equipped with a wireless tracker, and wherein the simulated OR environment is displayed through the VR goggle with position and size of the simulated endoscope monitor on the VR goggle display dependent on angle and position of the VR goggle.

A method designated B of preparing a physical model of a head and endoscope for surgical simulation includes importing into a workstation a radiological tomographic image stack of a head; segmenting the radiological tomographic image stack into hard tissue, soft tissue, and mucosal voxel models based at least in part on voxel intensity; and growing hard tissue, mucosal, and soft tissue regions in the hard tissue, soft tissue, and mucosal voxel models. The method continues with converting the hard tissue, soft tissue, and mucosal models into a hard tissue mesh model, a soft tissue mesh model, and a mucosal mesh model; repairing the mesh models; exporting the mesh models from the workstation and using a 3D printer and the hard tis-sue mesh model to print a physical hard tissue model; preparing a physical mucosal tissue model from the mucosal mesh model; and mounting the physical mucosal tissue model to the physical hard tissue model. The method also includes preparing a physical soft tissue model from the soft tissue mesh model; and mounting the physical soft tissue model to the physical hard tissue model to form a physical head model. The method also includes loading the mesh models into a display system adapted to render images of surfaces of the mesh models as viewed from an endoscope; mounting a tracker to the physical head model; and preparing an endoscope device with a tracker.

A method designated BA including the method designated B and including: tracking the endoscope device to determine a tracked endoscope position and orientation; determining a location and orientation of a tip of the endoscope device from the tracked endoscope position and orientation, the position of the tip of the endoscope device being within the physical head model; rendering images of surfaces of the mesh models as viewed from the tip of the endo-scope device; and displaying the images of surfaces of the mesh models.

A method designated BB including the method designated B or BA further includes mounting a tracker to a device representing a surgical tool; tracking the device representing a surgical tool to determine a location of a tip of the device representing a surgical tool; determining when the surgical tool is in view of the tip of the endoscope device; and when the surgical tool is in view of the tip of the endoscope device, rendering an image of a surgical tool as viewed from the tip of the endoscope device.

A method designated BC including the method designated B, BA, or BB further includes: tracking location and orientation of the physical head model; and registering the mucosal mesh model to the location and orientation of the physical head model.

A method designated BD including the method designated B, BA, BB, or BC where the rendering images of surfaces of the mesh models is performed with a 3D gaming engine.

A method designated BE including the method designated B, BA, BB, BC, or BD wherein the preparing a physical mucosal model is performed by casting using a mold that has been prepared from the mucosal mesh model by a method comprising 3D printing.

A method designated BF including the method designated B, BA, BB, BC, BD, or BE further includes identifying critical anatomic structures imaged in the radiological tomographic image stack and tagging those critical structures in a model of the mesh models.

A method designated BG includes the method designated B, BA, BB, BC, BD, BE, or BF and further includes generating alarms upon approach of a tip of the device representing a surgical tool to a critical structure tagged in the mesh model.

An endoscopic surgical simulation system designated C includes a physical head model; a tracking system configured to track location and angle of a device representing an endoscope and a device representing a surgical tool; a computer-aided design (CAD) model in a modeling, and display machine, the CAD model registered to a location of the physical head model and comprising CAD representations of structures corresponding to structures of the physical head model; with the modeling, and display machine being configured to track the device representing an endoscope and determine a location of a tip of the device representing an endoscope within a nasal cavity of the physical head model, and to determine a field of view of an endoscope located at the location of the tip of the device representing an endoscope. The modeling, and display machine is configured to track the device representing a surgical tool and determine a location of a tip of the device representing a surgical tool within the nasal cavity of the physical head model; and the modeling and display machine is configured to generate a video stream corresponding to a view of structures represented by the CAD model within the field of view. The modeling and display machine is also configured to superimpose on the video stream an image corresponding to a tip of a surgical tool when the location of a tip of the device representing a surgical tool is in a field of view of view.

An endoscopic surgical simulation system designated CA including the endoscopic surgical simulation system designated C wherein the CAD model includes models of a plurality of structures tagged as critical structures.

An endoscopic surgical simulation system designated CB including the endoscopic surgical simulation system designated C or CA further including a tracker coupled to the physical head model, and wherein the CAD model is registered to a location of the physical head model.

An endoscopic surgical simulation system designated CBA including the endoscopic surgical simulation system designated C, CA, or CB wherein the physical head model and CAD model are derived from computed tomography (CT) or magnetic resonance imaging (MRI) scans of a particular patient, the system configured for preoperative planning and practice for that particular patient.

An endoscopic surgical simulation system designated CBB including the endoscopic surgical simulation system designated C, CA, CB wherein there is a first physical head model and CAD model configured for a first task, and a second physical head model and CAD model configured for a second task, the second task of greater difficulty than the first task.

An endoscopic surgical simulation system designated CC including the endoscopic surgical simulation system designated C, CA, CB, CBA, or CBB wherein the modeling and display machine is configured to generate alarms upon approach of the location of a tip of the device representing a surgical tool to a structure tagged as a critical structure.

An endoscopic surgical simulation system designated CD including the endoscopic surgical simulation system designated C, CA, CB, CC, or CBA further including a model extraction workstation configured to extract three-dimensional mesh models from computed tomography (CT) or magnetic resonance imaging (MRI) radiographic images, and wherein the physical head model is generated by a method comprising 3D printing of extracted three-dimensional mesh models.

An endoscopic surgical simulation system designated CD including the endoscopic surgical simulation system designated C, CA, CB, CBA, CBB, or CC further including virtual reality (VR) goggles, the VR goggles equipped with a tracker.

An endoscopic surgical simulation system designated CE including the endoscopic surgical simulation system designated CD wherein the video stream corresponding to a view of structures represented by the CAD model within the field of view is displayed upon a display of the VR goggles.

An endoscopic surgical simulation system designated CF including the endoscopic surgical simulation system designated CE where the video steam corresponding to a view of structures represented by the CAD model is displayed on the VR goggles at a position dependent on location and orientation of the VR goggles.

It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A method of preparing a physical model of a head and endoscope for surgical simulation comprising:
   importing into a workstation a radiological tomographic image stack of a head;
   segmenting the radiological tomographic image stack into hard tissue, soft tissue, and mucosal voxel models based at least in part on voxel intensity;
   growing hard tissue, mucosal, and soft tissue regions in the hard tissue, soft tissue, and mucosal voxel models;
   converting the hard tissue, soft tissue, and mucosal models into a hard tissue mesh model, a soft tissue mesh model, and a mucosal mesh model;
   repairing the mesh models;
   exporting the mesh models from the workstation and using at least a 3D printer and the hard tissue mesh model to generate a physical head model by:
   printing a hard plastic physical hard tissue model from the hard tissue mesh model,
   preparing a resilient polymer physical mucosal tissue model from the mucosal mesh model;
   mounting the physical mucosal tissue model to the physical hard tissue model;
   preparing a resilient polymer physical soft tissue model from the soft tissue mesh model; and
   mounting the physical soft tissue model to the physical hard tissue model to form the physical head model;
   loading the mesh models into a display system adapted to render images of surfaces of the mesh models as viewed from an endoscope;
   mounting a tracker to the physical head model; and
   preparing an endoscope device with a tracker.

2. The method of claim 1 further comprising:
   tracking the endoscope device to determine a tracked endoscope position and orientation;
   determining a location and orientation of a tip of the endoscope device from the tracked endoscope position and orientation, the position of the tip of the endoscope device being within the physical head model;
   rendering images of surfaces of the mesh models as viewed from the tip of the endoscope device;
   displaying the images of surfaces of the mesh models.

3. The method of claim 2 further comprising:
   mounting a tracker to a device representing a surgical tool;
   tracking the device representing a surgical tool to determine a location of a tip of the device representing a surgical tool;
   determining when the surgical tool is in view of the tip of the endoscope device; and
   when the surgical tool is in view of the tip of the endoscope device, rendering an image of a surgical tool as viewed from the tip of the endoscope device.

4. The method of claim 3 further comprising:
   tracking location and orientation of the physical head model; and
   registering the mucosal mesh model to the location and orientation of the physical head model.

5. The method of claim 4 further comprising identifying critical anatomic structures imaged in the radiological tomographic image stack and tagging those critical structures in a model of the mesh models.

6. The method of claim 5 further comprising generating alarms upon approach of a tip of the device representing a surgical tool to a critical structure tagged in the mesh model.

7. The method of claim 6 further comprising generating a score based upon at least time of a trainee completing a task and approach of simulated endoscope tip and simulated tool tip to the critical structures tagged in the model.

8. The method of claim 6 wherein the physical head model and the endoscope device are configured to physically interact upon insertion of the endoscope device into a nasal cavity of the physical head model and thereby providing haptic feedback to a user, the haptic feedback approximating haptic feedback when the user inserts a real endoscope into a nasal cavity of a real human head.

9. The method of claim 3 where the rendering images of surfaces of the mesh models is performed with a 3D gaming engine.

10. The method of claim 9, further comprising identifying critical anatomic structures imaged in the radiological tomographic image stack and tagging those critical structures in a model of the mesh models.

11. The method of claim 10 further comprising generating alarms upon approach of a tip of the device representing a surgical tool to a critical structure tagged in the mesh model.

12. The method of claim 11 further comprising generating a score based upon at least time of a trainee completing a task and approach of simulated endoscope tip and simulated tool tip to the critical structures tagged in the model.

13. The method of claim 1 wherein the preparing a physical mucosal model is performed by casting using a mold that has been prepared from the mucosal mesh model by a method comprising 3D printing.

* * * * *